United States Patent [19]

Albaugh

[11] Patent Number: 5,198,545
[45] Date of Patent: Mar. 30, 1993

[54] PHARMACEUTICAL EPINEPHRINE-PILOCARPINE COMPOUNDS AND PROCESS OF PREPARATION THEREOF

[75] Inventor: Pamela Albaugh, Clinton, Conn.

[73] Assignee: Allergan, Inc., Irvine, Calif.

[21] Appl. No.: 773,059

[22] Filed: Oct. 8, 1991

Related U.S. Application Data

[63] Continuation of Ser. No. 434,914, Nov. 13, 1989, Pat. No. 5,055,467.

[51] Int. Cl.$^5$ ............................................. C07D 23/58
[52] U.S. Cl. ................................... 544/133; 548/314.7
[58] Field of Search ........................... 548/336; 544/133

[56] References Cited

U.S. PATENT DOCUMENTS 3,470,197  9/1969  Van Dyke, Jr. .................... 548/500

FOREIGN PATENT DOCUMENTS 0286903 10/1988 European Pat. Off. ............ 514/397

OTHER PUBLICATIONS

Koda et al., *J. Pharm. Sciences*, vol. 62, No. 12, pp. 2021-2023 (1973).

Gelatt et al., *Am. J. Vet. Res.*, vol. 44, No. 1, pp. 2018-2027 (1983).

Soderstrom, *American Journal of Ophthalmology*, vol. 107, pp. 465-470 (1989).

Drug and Therapeutics Bulletin, vol. 21 (22), pp. 85-88, (1983).

*Primary Examiner*—C. Warren Ivy
*Assistant Examiner*—Zinna N. Davis
*Attorney, Agent, or Firm*—Robert J. Baran; Howard R. Lambert; Martin A. Voet

[57] ABSTRACT

The present invention relates to new racemic and optically active compounds containing a first moiety derived from a pilocarpine compound in which the furanone ring of pilocarpine is replaced by a hetero-ring containing a secondary nitrogen hetero-atom, and a second moiety derived from an epinephrine compound or a β-adrenergic blocking compound, linked at the secondary nitrogen atom of the furanone-replacing hetero-ring of the pilocarpine compound and at the hydroxyl group of the epinephrine compound or of the β-adrenergic blocking compound, via a carbonyl linker, and pharmaceutically acceptable acid addition salts thereof.

The new compounds of the present invention are potent ocular hypotensives exhibiting minimal deleterious pupillary effects.

3 Claims, 4 Drawing Sheets

(REACTION SCHEME)

PHARMACEUTICAL EPINEPHRINE-PILOCARPINE COMPOUNDS AND PROCESS OF PREPARATION THEREOF

This is a continuation of copending application U.S. Ser. No. 07/434,914 filed on Nov. 13, 1989 now U.S. Pat. No. 5,055,467.

FIELD OF THE INVENTION

The present invention relates to new chemical compounds having valuable pharmacological properties. More particularly, the present invention concerns novel, pharmaceutically active compounds that contain a moiety derived from an epinephrine derivative or a β-blocker linked to another moiety derived from a pilocarpine derivative.

BACKGROUND OF THE INVENTION

Epinephrine (also called adrenaline), by its most commonly used chemical name 4-[1-hydroxy-2-(methylamino)ethyl]-1,2-benzenediol, is a known, commercially available compound. Its l-form has adrenergic properties, and together with its dipivalate [di(trimethylacetate)] ester derivative, propine, is a clinically useful anti-glaucoma agent. These compounds also cause mydriasis, an excessive dilation of the pupil of the patient's eye upon administration.

Beta-adrenergic blocking agents (β-blockers) are structurally similar to epinephrine derivatives and, indeed, their certain representatives such as 1-[(1,1-dimethylethyl)-amino]-3-{[4-morpholinyl-1,2,5-thiadiazol-3-yl]oxy}-2-propanol (timolol); 1-{4-[2-(cyclopropylmethoxy)ethyl]phenoxy}-3-[(1-methylethyl)amino]-2-propanol (betaxolol) and 5-[3-(terbutylamino)-2-hydroxypropoxy]-3,4-dihydro-1(2H) -nathalenone (bunolol), lower intraocular pressure.

Typical representatives of another class of known anti-glaucoma agents (muscarinics) are pilocarpine [(3S,4R)-3-ethyl-4-[(1-methyl-1H-imidazol-5-yl)methyl]-3,4-dihydro-2(3H)-furanone], and its pyrrolidinone derivative, (3R, 4R) 3-ethyl-4-[(1-methyl-1H-imidazole-5-yl)methyl]-2-pyrrolidinone. The latter compound, together with other, 1-alkyl substituted derivatives, is disclosed in the U.S. Pat. No. 3,470,197 See also Koda, et al., *J. Pharm. Sci.* 62, 2021 (1973) who describe certain of these compounds as possessing cholinergic activity.

Muscarinics lower intraocular pressure via contraction of the ciliary muscle, and as a side-effect, also cause simultaneous contraction of the iris muscle leading to miosis in the patient's eye.

SUMMARY OF THE INVENTION

The present invention relates to new pharmaceuticals which are formed by coupling a pilocarpine compound and an epinephrine compound or a β-adrenergic blocking compound, via a linking carbonyl group.

More particularly, the present invention concerns new racemic and optically active compounds containing a first moiety derived from a pilocarpine compound in which the furanone ring of pilocarpine is replaced by a hetero-ring containing a secondary nitrogen heteroatom, and a second moiety derived from an epinephrine compound or a β-adrenergic blocking compound, linked at the secondary nitrogen atom of the furanone-replacing hetero-ring of the pilocarpine compound and at the hydroxyl group of the epinephrine compound or of the β-adrenergic blocking compound, via a carbonyl linker, and pharmaceutically acceptable acid addition salts thereof.

The epinephrine compound may contain more hydroxyl groups, but the linking carbonyl group is always attached to the hydroxyl in the 1-position.

A preferred group of the compounds of the present invention is encompassed by formula (I)

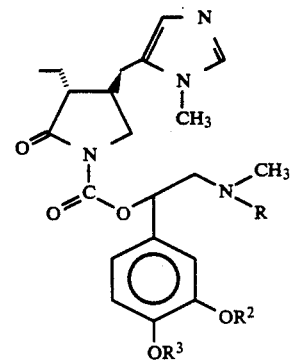

wherein

R is hydrogen or a —COOR$^1$ group,

R$^2$ and R$^3$ each independently represent hydrogen or a —COR$^4$ group,

R$^1$ and R$^4$ independently are substituted or unsubstituted alkyl groups, and pharmaceutically acceptable acid addition salts thereof.

In another aspect, the present invention relates to a process for the preparation of the above-defined racemic and optically active compounds by linking a first moiety derived from a pilocarpine compound, and a second moiety derived from an epinephrine compound or a β-adrenergic blocking compound, at the heteroatom of the oxo group-carrying ring of the pilocarpine compound and at the hydroxyl group of the epinephrine compound or of the β-adrenergic blocking compound, via a carbonyl linker.

Compounds of formula (I), wherein R and R$^1$-R$^4$ are as hereinabove defined, can be prepared by coupling a compound of the formula (II):

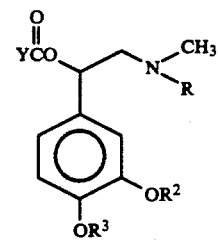

wherein R, R$^2$ and R$^3$ have the same meanings as hereinabove described, and

Y is a leaving group, with (3R,4 R)-3-ethyl-4-[(1-methyl-1H-imidazol-5-yl)methyl]-2-pyrrolidinone of the formula (III):

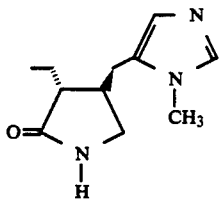

If desired, the obtained compounds can be converted into or freed from their respective acid addition salts by methods known per se.

If racemic starting compound(s) is (are) employed, compounds of the formula (I) are obtained as racemates that can be resolved into the respective enantiomers by methods known in the art. [Jacques, J.; Collet, A.; Wileu, S. H. "Enantiomers, Racemates and Resolutions"; Wiley, N.Y. 1981]

Other compounds, containing a β-blocker-derived moiety in place of the epinephrine moiety can be prepared in an analogous manner, starting from a compound of formula (III) as hereinabove defined, and from an appropriately derivatized β-adrenergic blocking agent.

The new compounds of the present invention are potent ocular hypotensives exhibiting minimal deleterious pupillary effects. Hence, they are targeted as valuable antiglaucoma agents that are more effective than either the know pilocarpine-type compounds or the known epinephrine-type compounds. Accordingly, in a further aspect, the present invention relates to pharmaceutical compositions containing these compounds or their pharmaceutically acceptable salts, as active ingredients.

Figure 6:
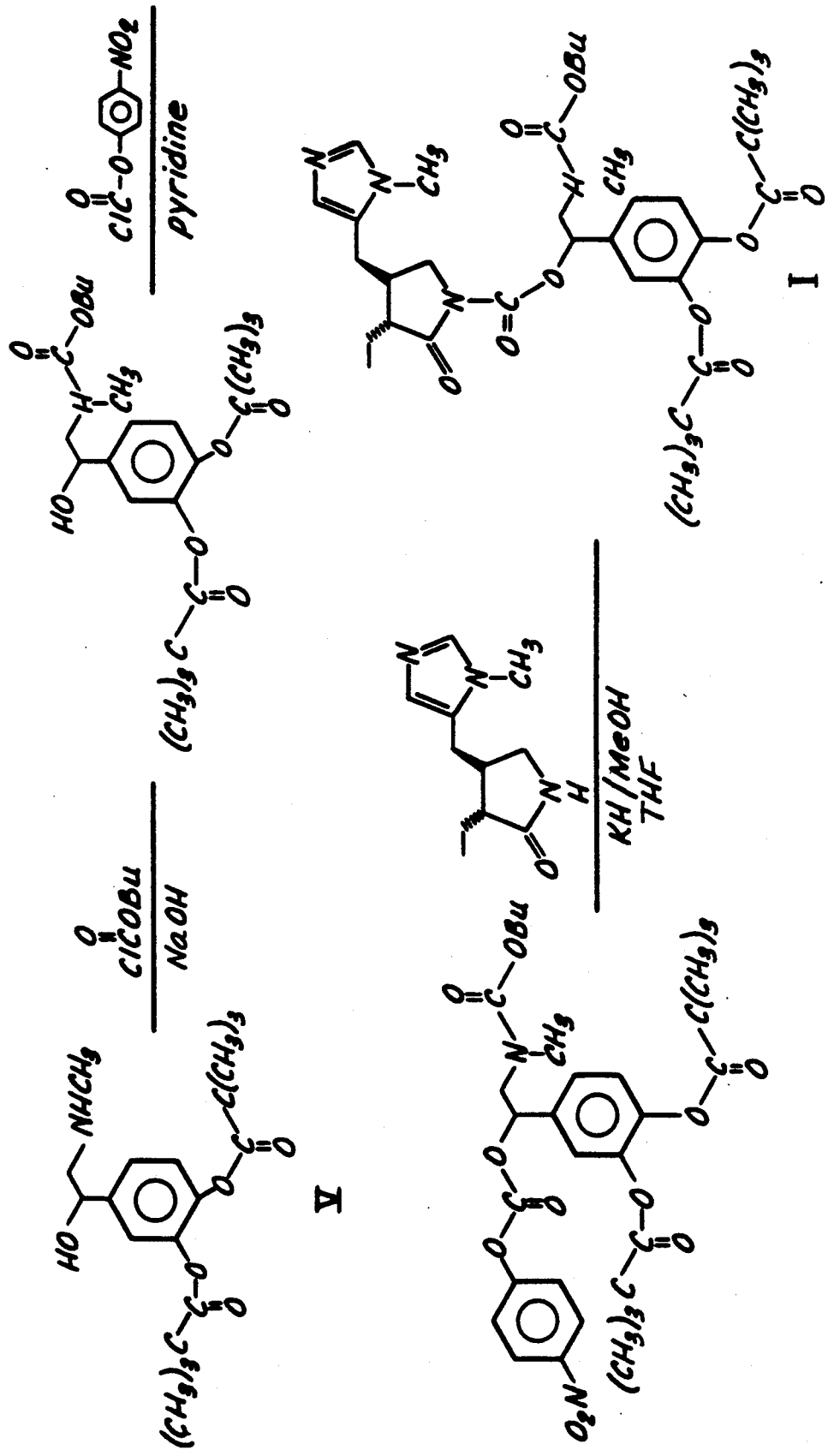

The FIG. 6 (Reaction Scheme) illustrates a typical reaction route for the synthesis of a compound of formula (I), starting from a corresponding compound of formula (IV).

DETAILED DESCRIPTION OF THE INVENTION

The term "pilocarpine compound" is used to refer to

1. Definitions

The term "pilocarpine compound" is used to refer to pilocarpine derivatives in which the furanone ring of pilocarpine is replaced by a secondary nitrogen-containing heterocyclic ring, which derivatives are therefore capable of forming a chemical bond with the carbonyl linking group at the secondary nitrogen, and to structurally related compounds, provided that they form ophthalmically active compounds with moieties derived from epinephrine compounds or β-blocking compounds, as hereinafter defined In particular, the term includes compounds which contain a secondary nitrogen-containing hetero-ring carrying an oxo group, such as a pyrrolidinone ring, in place of the furanone ring of pilocarpine, and yield compounds lowering intraocular pressure when coupled with the epinephrine or β-blocking compounds defined hereinbelow. Typically, these pilocarpine compounds are themselves ocular hypotensives. A typical representative of the pilocarpine derivatives included by this term is 3-ethyl-4-[(1-methyl-1H-imidazol-5-yl)methyl]-2-pyrrolidinone.

The term "opthalmically active" is used to refer to pharmaceutically active compounds that penetrate the eye and are useful in the treatment of ocular diseases. Preferably such compounds lower intraocular pressure, and ar, therefore, useful as anti-glaucoma agents.

The term "epinephrine compound" as used herein, refers to epinephrine and epinephrine derivatives that when linked to pilocarpine compounds, as hereinabove defined, yield ophthalmically active compounds. Typically, the epinephrine compounds are themselves ophthalmically active, in particular are ocular hypotensives, being useful in the treatment of glaucoma. A typical group of these compounds is represented by formula (II), wherein the substituents are as hereinabove defined.

The term "β-adrenergic blocking compounds" and synonymous expressions, are preferably used to refer to those β-blockers that penetrate the eye, and are, therefore, suitable for ophthalmic use.

In the definition of $R^1$ and $R^4$, the alkyl groups may be straight or branched chained, preferably containing up to 6, more preferably up to 4 carbon atoms. Typical representatives of the alkyl groups include, for example, methyl, ethyl, n- and i-propyl, n-, sec-, i- and tert-butyl, n- and i-pentyl groups.

All of these alkyl groups may carry one or more identical or different substituents, such as alkyl, alkenyl or alkinyl, alkoxy group, halogens, etc.

In the compounds of formula (I), the linking group is a carbonyl group that is subject to recognition and cleavage by an esterase, for example.

Y may be any leaving group conventionally used in nucleophilic substitution reactions in combination with secondary or tertiary amines. Such groups are well known in peptide chemistry, and include, but are not restricted to ester groups, halogen atoms and nitriles. The leaving group is preferably derived from active esters, such as p-nitrophenyl ester.

2. Description of Preferred Embodiments

In a preferred group of the compounds according to the present invention, the pilocarpine moiety is derived from a pyrrolidinone derivative of pilocarpine: (3R,4R) 3-ethyl-4-[(1-methyl-1H-imidazole-5-yl)methyl]-2-pyrrolidinone.

Further preferred compounds are those in which the epinephrine moiety is derived from 4-[1-hydroxy-2-(methylamino)ethyl]-1,2-benzenediol or the dipivalate ester of this compound.

Compounds wherein the β-adrenergic blocking compound is selected from the group consisting of 1-[(1,1-dimethylethyl)-amino]-3-{[4-morpholinyl-1,2,5-thiadiazol-3-yl]oxy}-2-propanol (timolol) ; 1-{4-[2-(cyclopropylmethoxy)ethyl]phenoxy}-3-[(1-methylethyl)amino]-2-propanol (betaxolol) and 5-[3-(tertbutylamino)-2-hydroxypropoxy]-3,4-dihydro-1(2H)-naphthalenone (bunolol) are also preferred.

The most preferred compounds according to the present invention are encompassed by formula (I), wherein the substituents are as hereinabove defined One of the starting compounds in the synthesis of the compounds of the present invention, including compounds of formula (I) is (3R, 4R) 3-ethyl-4-[(l-methyl-1H-imidazole-5-yl)methyl]-2-pyrrolidinone [see formula (III)]. This compound can be prepared by reaction of pilocarpine with ammonia in a suitable solvent inert under the reaction conditions, essentially following the procedure described in the U.S. Pat. No. 3,470,197. The preferred solvent is ammonia itself. The reaction is a single step reaction and is conveniently performed in an autoclave, or in a high-pressure reactor.

Starting compounds of formula (II) can be obtained from compounds of formula (IV)

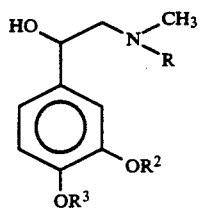

(the substituents are as hereinabove defined) by reaction with suitable reactants carrying the desired linking carbonyl group and a leaving group (Y). For example, the intermediate compounds of formula (IV) can be reacted with a suitable active ester to yield the desired starting compounds of formula (II). The compounds of formula (IV) are commercially available or can be easily prepared from commercially available compounds. For example, 3,4-dihydroxy-alpha-[(methylamino)methyl]-benzyl alcohol 3,4-dipivalate is known as dipivefrin and ophthalmic solutions containing its hydrochloride are commercially available (Propine ®). Dipivefrin can subsequently be converted into the corresponding compounds of formula (IV) in which R is a COOR$^1$ group (R$^1$ is as hereinabove defined) by well known reactions of organic chemistry, for example by reaction with the respective esters of a haloformic, such as chloroformic acid. According to a particularly preferred embodiment, an N-substituted compound of formula (IV) (R is other than hydrogen) is subsequently reacted with p-nitrophenyl-chloroformate in the presence of pyridine, in tetrahydrofuran (THF) solvent, at ambient temperature. The reaction affords a compound of formula (II) in which Y is a p-nitro-phenolate group. Other carboxy-ester derivatives can be prepared in an analogous manner.

A typical synthesis for the preparation of the compounds of the present invention is illustrated in the enclosed Reaction Scheme.

The β-blockers that may be reacted with the pilocarpine starting compounds, preferably with compounds of formula (III), are commercially available compounds.

In the coupling reaction providing the target compounds of formula (I), the anion of the compounds of formula (III) is reacted with the respective compounds of formula (II), or with the β-blocker reaction partners. Before coupling, the anion of the compounds of formula (III) is prepared usually via treatment with potassium hydride and catalytic amount of methanol, in tetrahydrofuran (THF) at 0° C.

The coupling reaction is preferably carried out in a solvent, inert under the reaction conditions such as tetrahydrofuran, at a temperature between about 0° C. and room temperature The reaction time usually is several hours.

A typical reaction route for the synthesis of a compound of formula (I), starting from a corresponding compound of formula (V) is shown in Reaction Scheme B.

If desired, an obtained compound, such as a compound of formula (I), wherein R, R$^2$ and R$^3$ have the same meanings as defined above, is converted into its pharmaceutically acceptable acid addition salts, or an obtained acid addition salt is converted into the respective free compound or into another, pharmaceutically acceptable acid addition salt, by methods known in the art.

Acid addition salts may be formed with suitable mineral or organic acids, such as hydrochloric acid, hydrobromic acid, sulfuric acid, acetic acid, propionic acid, butyric acid, caproic acid, lactic acid, oxalic acid, malonic acid, malic acid, citric acid, etc., and can be prepared by methods known per se. The foreseeable requirement is that they be pharmaceutically acceptable for administration to man.

Compounds of formula (I) in which at least one of R, R$^2$ and R$^3$ is hydrogen can be converted into other compounds of the same general structure carrying other substituents in these positions. Similarly, substituted compounds may easily be converted into the respective compounds of formula (I) in which R, R$^2$ and/or R$^3$ is hydrogen.

Methods for resolution of racemic compounds of the formula (I), and other adducts according to the present invention, are known in the art, and are disclosed in ordinary textbooks of organic chemistry, such as Jacques, J.; Collt, A.; Wileu, S. H., supra.

The new compounds of the present invention exhibit valuable pharmaceutical properties. More particularly, these compounds are potent anti-glaucoma gents that are more effective than the clinically useful pilocarpine- and epinephrine-type starting compounds used for their preparation. Furthermore, in the new compounds according to the present invention, the undesirable side-effects of the known anti-glaucoma agents currently used in clinical practice are significantly diminished Pharmaceutical compositions may be prepared by combining a therapeutically efficient amount of at least one compound according to the present invention, or a pharmaceutically acceptable acid addition salt thereof, as an active ingredient, with conventional pharmaceutical excipients. Preferably, at least one of the active ingredients is a compound of formula (I), wherein the substituents are as hereinabove defined. The therapeutically efficient amount typically is between about 0.1 and about 5% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives and stabilizers.

Preferred preservatives that may be used in the pharmaceutical compositions of the present invention include, but are not limited to, benzalkonium chloride, chlorobutanol, thimerosal, phenylmercuric acetate and phenylmercuric nitrate. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable opthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place or in conjunction with it.

The ingredients are usually used in the following amounts:

| Ingredient | Amount (% w/v) |
|---|---|
| active ingredient | about 0.1–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| purified water | as needed to make 100% |

Typical ophthalmic preparation of the present invention is illustrated in Example 2.

Further details of the invention are illustrated by the following, non-limiting examples.

EXAMPLE 1

Test of Pharmacological Activity

Since muscarinics are known in the art not to lower intraocular pressure (IOP) in rabbits, we followed miosis, a known side-effect of such compounds, to indicate topical activity.

Methods

The test compound was topically applied in volumes of 25 μl (rabbits) or 10 μl (owl monkeys). Solutions with active ingredient concentrations ranging from 0.5% to 4% were tested. Pupil diameter was measured at times 0, 0.5, 1, 2, 3, 4, 5 and 6 hours after treatment. Normal saline was used as vehicle control, and pilocarpine (0.5–1%) as positive control. Intraocular pressure was also measured at the above times after treatment with selected compounds. The test compound was initially dissolved in 0.01N acetic acid and brought to the desired final volume with normal saline. The pH of all test solutions was adjusted to 5.

Results

Corneal penetration was determined by measuring miosis following topical application. Effect of the test compound on pupil size in rabbits is shown in Table 1.

TABLE 1

| CONCENTRATION (%) | DECREASE IN PUPIL DIAMETER[a] (mm.) | TIME TO WORK[b] (hrs.) | DURATION[c] (hrs.) |
|---|---|---|---|
| 1 | −2.3 | 1 | 6+ |

[a]Maximum decrease in pupil diameter
[b]Time the maximum effect was obtained
[c]Time when there was at least 0.5 mm decrease in pupil diameter or maximum response was maintained.

Figure 1:
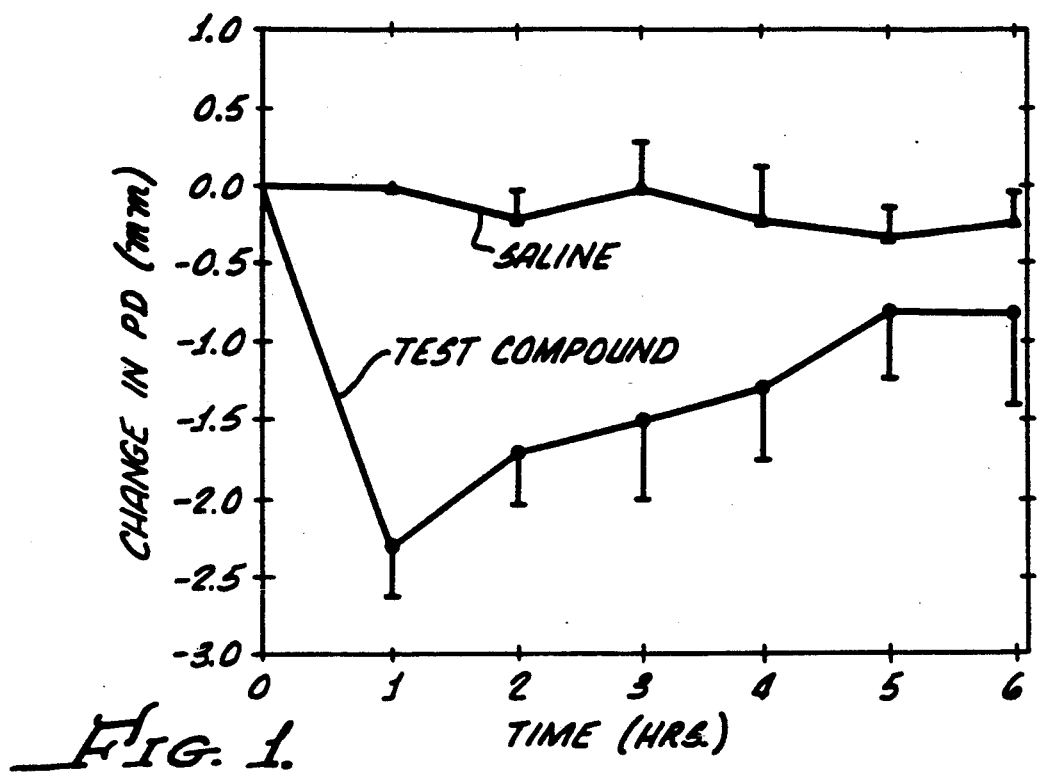
FIG. 1 shows the effect of a 1% solution of the test compound on pupil diameter in rabbits, at different times following topical application.
Figure 2:
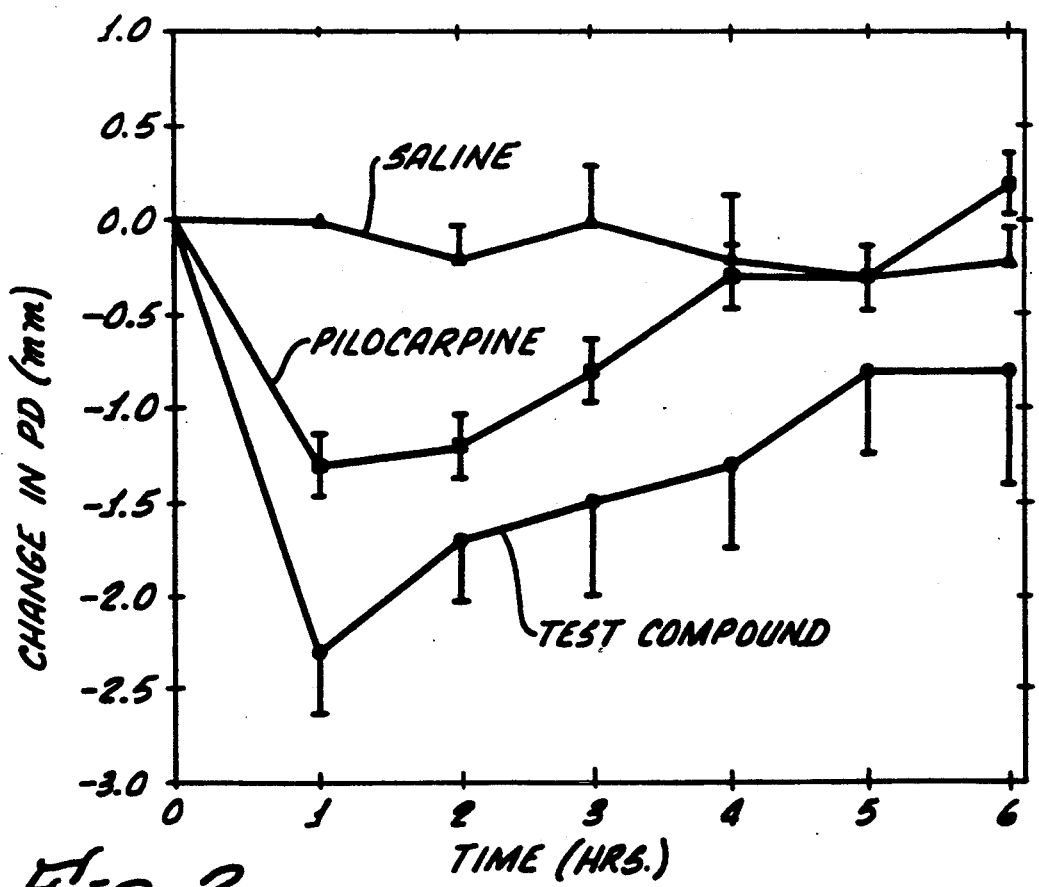
FIG. 2 illustrates the effect of 1% solutions of the test compound and pilocarpine on pupil diameter in rabbits, at different times following topical application.

In rabbits, in 1% solution, the compound caused miosis that was greater than that of 1% pilocarpine solution, suggesting greater penetration (FIGS. 1 and 2). However, the pattern of recovery of pupil size was similar to pilocarpine. This shorter duration of action may be due to the mydriatic effect caused by epinephrine moiety of the prodrug.

Figure 3:
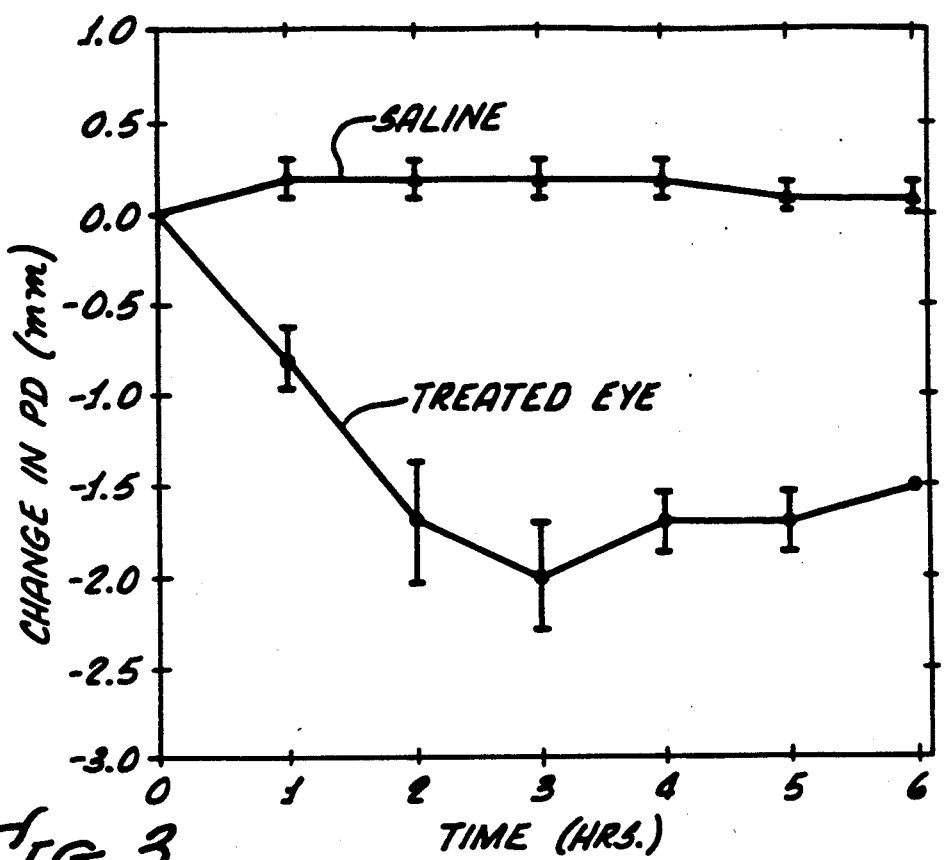
FIG. 3 illustrates the effect of a 0.5% solution of the test compound on pupil diameter in owl monkeys, at different times following topical application.

The effect of the test compound on pupil size in owl monkeys was again less than seen in rabbits. Maximum effect was obtained at 3 hours and was maintained up to 6 hours (FIG. 3).

Figure 4:
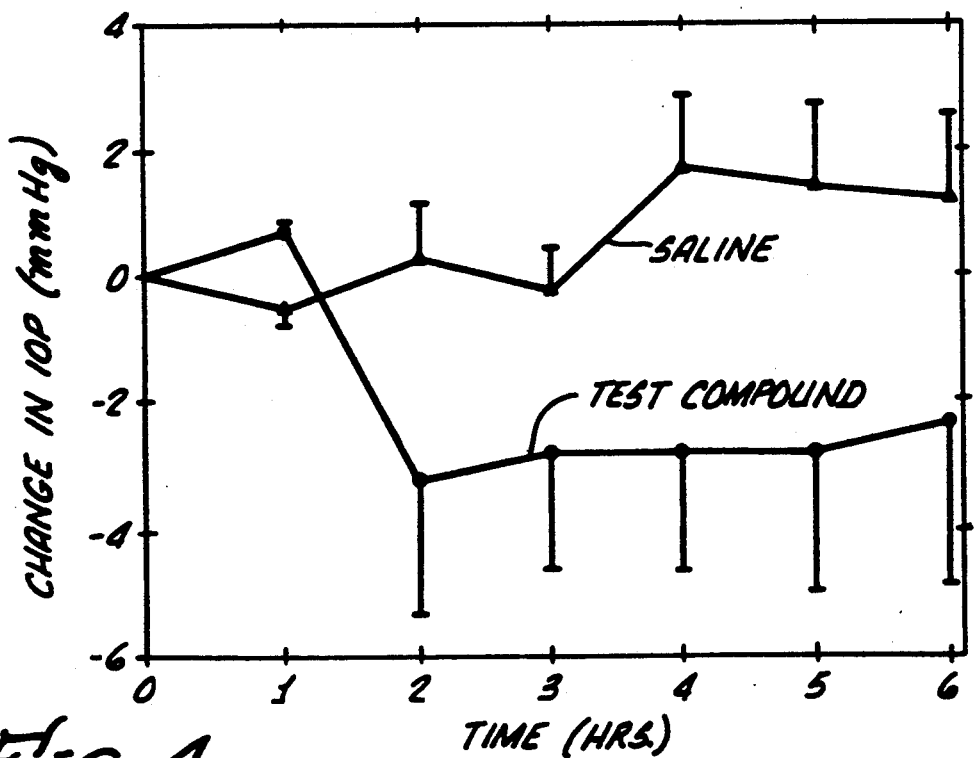
FIG. 4 illustrates the effect of a 1% solution of the test compound on intraocular pressure in rabbits, at different times following topical application.
Figure 5:
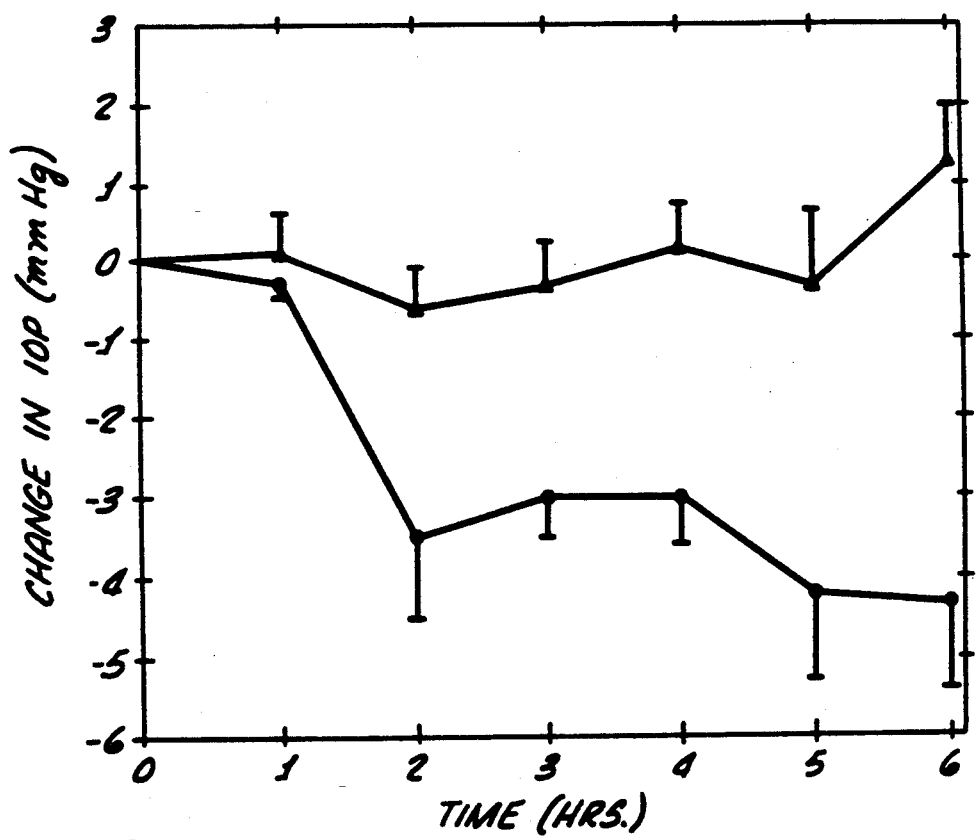
FIG. 5 shows the effect of a 0.5% solution of the test compound on intraocular pressure in owl monkeys, at different times following topical application.

Effect on IOP:

In rabbits, IOP was reduced by about 4 mmHg with 1% test compound at 2 hours and lasted longer than 6 hours (FIG. 4). A similar effect was also observed in owl monkeys (FIG. 5). This compound had effect in the contralateral eye causing a reduction of 2-3 mHg decrease in IOP.

EXAMPLE 2

Preparation of (3R, 4R)-1-carbo-[3,4-dipivaloyl-α-(N-carbobutyryloxy-N-methyl-aminomethyl)benzoxy[-3-ethyl-4[(1-methyl-1H-imidazol-5yl)methyl]-2-pyrrolidinone To a solution of (3R,4R)-3-ethyl-4-[(1-methyl-1H-imidazole-5-yl)methyl]-2-pyrrolidinone, (27 mg, 0.13 mmol) in THF (2 mL) at room temperature (RT) was added potassium hydride (7 mg, 0.17 mmol) and methanol (4.0×10⁻⁴ mg, 0.01 mmol). The reaction mixture was stirred at RT for 30 min., then cooled at 0° C., and 0-(4-nitrophenyl)-0′-[3,4-dipivaloyl-α-(N-carbobutyryloxy-N-methyl-aminomethyl)benzyl]carbonate (102 mg, 0.165 mmol) was added. The reaction mixture was stirred at 0° C. for 75 min., then warmed to RT and stirred for 4.75 hours. The reaction was quenched with saturated NaHCO$_3$, extracted twice with CH$_2$Cl$_2$, dried (Na$_2$SO$_4$), filtered, concentrated and the residue was chromatographed on silica gel (5% MeOH saturated with NH$_3$/CHCl$_3$) to give 57.6 mg of a diastereomeric mixture of the title compound as a lemon yellow oil (65%).

$^1$H NMR (300 MHz, CDCl$_3$): 7.43 (s, 1H), 7.32–7.13 (m, 3H), 6.85 (s, 1H), 6.03–6.02 and 5.98–5.96 (m, 1H diastereomeric, 4.09–4.05 (m, 2H), 3.94–3.88 (m, 1H), 3.72–3.64 (m, 2H), 3.57 (s, 3H), 3.41–3.36 (m, 1H), 3.01–2.94 (m,3H diastereomeric), 2.85–280 (m, 1H), 2.70–2.62 (m, 1H), 2.37–2.27 (m, 2H), 1.75–1.71 (m, 2H), 1.65–1.58 (m, 2H), 1.44–1.32 (m, 2H), 1.35 (s, 9H), 1.34 (s, 9H), 1.04–0.93 (m, 6H). $^{13}$C NMR (75 MHz, CDCl$_3$): 175.6, 175.5, 174.4, 174.1, 156.6, 156.2, 150.7, 150.6, 142.7, 142.6, 142.5, 138.1, 128.2, 127.1, 124.6, 123.6, 121.9, 121.8, 121.75, 65.4, 65.3, 54.0, 53.98, 53.56, 53.4, 50.3, 49.6, 39.0, 38.98, 36.4, 35.8, 34.5, 31.2, 31.1, 30.9, 27.7, 27.1, 22.2, 19.1, 19.0, 13.6, 10.9. High resolution mass spec. found 684.3749 for $C_{36}H_{52}N_4O_9$, $\Delta 1.5$ mmu A. To a solution of 3,4-dipivaloyl-α-(N-carbobutyryloxy-N-methyl-aminomethyl) benzyl alcohol (134 mg, 0.30 mmol) and pyridine (26.4 mg, 0.33 mmol) in THF (5 mL) at RT was added 4-nitrophenyl chloroformate (67 mg, 0.33 mmol), and the mixture was stirred at RT for 23.25 hours. The mixture was concentrated in vacuo and the residue was chromatographed on silica gel (1% MeOH saturated with $NH_3/CHCl_3$) to give 102.4 mg of a diastereomeric mixture of 0-(4-nitrophenyl)-0'-[3,4-dipivaloyl-α-(N-carbobutyryloxy-N-methyl-aminomethyl)benzyl] carbonate as a crystalline solid.

$^1$H NMR (300 MHz, $CDCl_3$): 8.27 (d, J=8.9 Hz, 2H), 7.38 (d, J=8.9 Hz, 2H), 7.31-7.18 (m, 3H), 6.0-5.96, 5.92-5.88 (m, 1H diastereomieric), 4.13 (t, J=6.6 Hz, 2H), 3.02, 2.94 (s, 3H diastereomeric), 1.66-1.62 (m, 2H), 1.44-1.35 (m, 2H), 1.37 (s, 9H) 1.35 (s, 9H), 0.97-0.93 (m, 3H). $^{13}$C NMR (75 MHz, $CDCl_3$): 176.1, 176.0, 157.1, 156.6, 155.7, 155.6, 151.9, 145.7, 143.4, 143.2, 135.1, 135.0, 125.5, 124.6, 124.1, 122.0, 121.8, 78.9, 78.7, 65.6, 54.4, 53.8, 39.0, 36.2, 35.9, 30.9, 27.0, 19.0, 13.5. High resolution mass spec. found 634.2964 for $C_{31}H_{44}N_3O_{11}$, 1.2 mmu.

B. To a 0°-5° C. solution of dipivaloyl epinephrine hydrochloride (776 mg, 2.0 mmol) in aqueous NaOH (50 mL) at pH 11 was added n-butyl chloroformate (408 mg, 3.0 mmol) over eight minutes. The mixture was maintained at pH 11 during the addition by adding aqueous NaOH as required. The reaction was stirred at 0° C.-5° C. for 30 min., then warmed to RT. After 1.75 hr., the mixture was diluted with $H_2O$, the pH was adjusted to basic with aqueous NaOH, the mixture was extracted twice with ethyl acetate, the combined organic extracts were dried ($Na_2SO_4$), filtered, concentrated and the residue was chromatographed on silica gel (5% MeOH saturated with $NH_3/CHCl_3$) to give 821.4 mg of a diastereomeric mixture of 3,4-dipivaloyl-α(N-carbobutyryloxy-N-methylaminomethyl)benzyl alcohol as a colorless oil (91%).

$^1$H NMR (300 MHz, $CDCl_3$): 7.18-7.02 (m, 3H), 4.9-4.8 (m, 1H, diastereomeric), 4.06-4.02 (m, 2H), 3.4 (d, J=5.4 Hz, 2H), 2.87 and 2.77 (bs, 3H, diastereomeric), 1.6-1.5 (m, 2H), 1.38-1.07 (m, 2H), 1.29 (s, 9H), 0.89 (t, J=7.3 Hz, 3H). $^{13}$C NMR (75 MHz, $CDCl_3$): 176.2, 176.15, 158.7, 142.7, 141.9, 141.1, 123.7, 123.3, 120.9, 72.5, 72.2, 65.6, 65.5, 57.5, 38.9, 36.1, 30.8, 26.9, 18.8, 13.4.

The foregoing description details specific methods that can be employed to practice the present invention. However, it is apparent for one of ordinary skill in the art that further compounds with the desired pharmacological properties can be prepared in an analogous manner, and that the disclosed compounds can also be obtained from different starting compounds via different chemical reactions. Thus, however detailed the foregoing may appear in text, it should not be construed as limiting the overall scope hereof; rather, the ambit of the present invention is to be governed only by the lawful construction of the appended claims.

I claim:

1. Process for the preparation of racemic and optically active compounds which comprises linking a first moiety derived from a pilocarpine compound in which the furanone ring of pilocarpine is replaced by a hetero-ring containing a secondary nitrogen hetero-atom, and a second moiety derived from an epinephrine compound or a β-adrenergic blocking compound consisting of timolol, hetaxolol, or bunolol, at said secondary nitrogen atom of the furanone-replacing hetero-ring of said pilocarpine compound and at the hydroxyl group of said epinephrine compound or of said β-adrenergic blocking compound, via a carbonyl linker.

2. A process according to claim 1, wherein said pilocarpine compound is (3R,4R) 3-ethyl-4-[(1-methyl-1H-imidazol-5-yl)methyl]-2-pyrrolidinone.

3. A process according to claim 1, further comprising the step of converting said compound into a pharmaceutically acceptable acid addition salt thereof.

* * * * *